United States Patent
Matsuomoto et al.

(10) Patent No.: US 7,381,543 B2
(45) Date of Patent: Jun. 3, 2008

(54) TAB1 PROTEIN AND DNA CODING THEREFORE

(75) Inventors: Kunihiro Matsuomoto, Nagoya (JP); Eisuke Nishida, Kyoto (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 78 days.

(21) Appl. No.: 11/180,911

(22) Filed: Jul. 14, 2005

(65) Prior Publication Data

US 2006/0172380 A1    Aug. 3, 2006

Related U.S. Application Data

(60) Continuation of application No. 10/123,427, filed on Apr. 17, 2002, now abandoned, which is a division of application No. 09/688,701, filed on Oct. 17, 2000, now abandoned, which is a division of application No. 09/406,854, filed on Sep. 29, 1999, now Pat. No. 6,140,042, which is a division of application No. 08/752,891, filed on Nov. 20, 1996, now Pat. No. 5,837,819.

(30) Foreign Application Priority Data

Apr. 24, 1996  (JP) .................................. 8-126282
Oct. 28, 1996  (JP) .................................. 8-300856

(51) Int. Cl.
*C12N 15/00*  (2006.01)
*C07H 21/04*  (2006.01)

(52) U.S. Cl. ...................... 435/69.1; 435/6; 435/320.1; 536/23.1

(58) Field of Classification Search ................... None
See application file for complete search history.

(56) References Cited

FOREIGN PATENT DOCUMENTS

JP         2003-135070         5/2003

OTHER PUBLICATIONS

Hiroaki Sakurai et al. "Functional Interactions of Transforming Growth Factor β-activated Kinase 1 with IκB Kinase to Stimulate NF-κB Activation", The Journal of Biological Chemistry, vol. 274, No. 15, Issue of Apr. 9, 1999, pp. 10641-10648, 1999.
Shibuya et al., "Is AMK-1 a Transfer Molecule Involved in TGF-β Signal Transduction," *68th Meeting of Japanese Society* (Sep. 15-18, 1995; Summary Published Jul. 25, 1995 Sendai, Japan).
Nishida, et al., "Signaling Pathways and Functions of the MAP Kinase Superfamily," *54th Meeting of Japanese Cancer Association*, (Oct. 3-5, 1995 Koyoto, Japan).
Irie et al., "A Novel Member of MAPKK, TAKI, May Function As a Monitor in TGF-β Signal Transduction," *18th Meeting of Japanese Molecular Biochemistry Society S21-4 and 2E11*, (Dec. 6-9, 1995, Nagoya, Japan).
Yamaguchi et al., "Identification of a Member of the MAPKK Family as a Potential Mediator of TGF-β Signal Transduction," *Science 270:2008-11*, (1995).
Shibuya et al. "TAB1: An Activator of the TAK1 MAPKKK in TGF-β Signal Transduction," *Science 272:1179-82*, (1996).

*Primary Examiner*—Sean McGarry
(74) *Attorney, Agent, or Firm*—Foley & Lardner LLP

(57) ABSTRACT

TAB1 protein having activity which activates factor TAK1 in the TGF-β signaling pathway, and having the amino acid sequence shown in FIG. 1.

1 Claim, 8 Drawing Sheets

| TAK1 | TAB |
|---|---|
| TAK1ΔN | GAD |
| TAK1 | GAD |
| TAK1 | GAD-TAB1 |
| vector | GAD-TAB1 |

Fig. 4

```
MAAQRRSLLQSEQQPSWIDDLPLCHLSGVGSASNRSYSADGKGIESHPPEDSWLKFRSEN    60
NCFLYGVFNGYDGCNRVTNFVAQRLSAELLLGQLNAEHAEADVRRVLLQAFDVVERSFLES   120
IDDALAEKASLQSQLPEGVPQHQLPPQYQKILERLKTLEREISGGAMAVVAVLLNNKLYV    180
ANVGTNRALLCKSTVDGLQVTQLNVDHTTENEDELFRLSQLGLDAGKIKQVGIICGQEST   240
RRIGDYKVKYGYTDIDLLSAAKSKPIIAEPEIHGAQPLDGVTGFLVLMSEGLYKALEAAH   300
GPGQANQEIAAMIDTEFAKQTSLDAVAQAVVDRVKRIHSDTFASGGERARFCPRHEDMTL   360
LVRNFGYPLGEMSQPTPSPAPAAGGRVYPVSVPYSSAQSTSKTSVTLSLVMPSGQMVNG    420
AHSASTLDEATPTLTN QSPTLTLQSTNTHTQSSSSSDGGLFRSRPAHSLPPGEDGRVEP    480
                 **  .  **  ******
               TAK1   1  MSTASAASSSSSSASEMIEAPSQ

YVDFAEFYRLWSVDHGEQSVVTAP                                       504
```

Fig.6
1  2  3  4
 ◄ Myc-TAB1
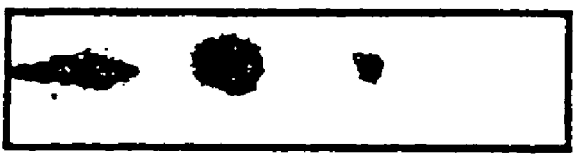 ◄ HA-TAK1

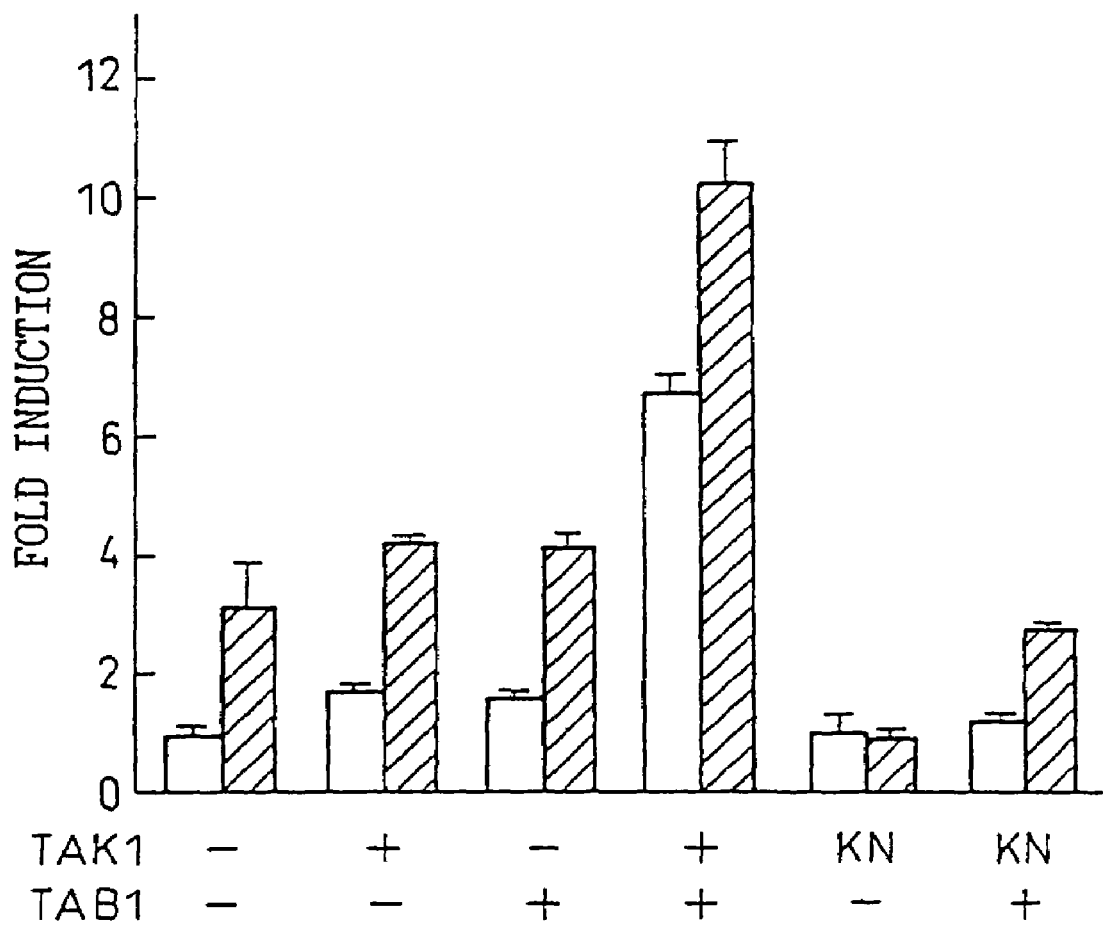

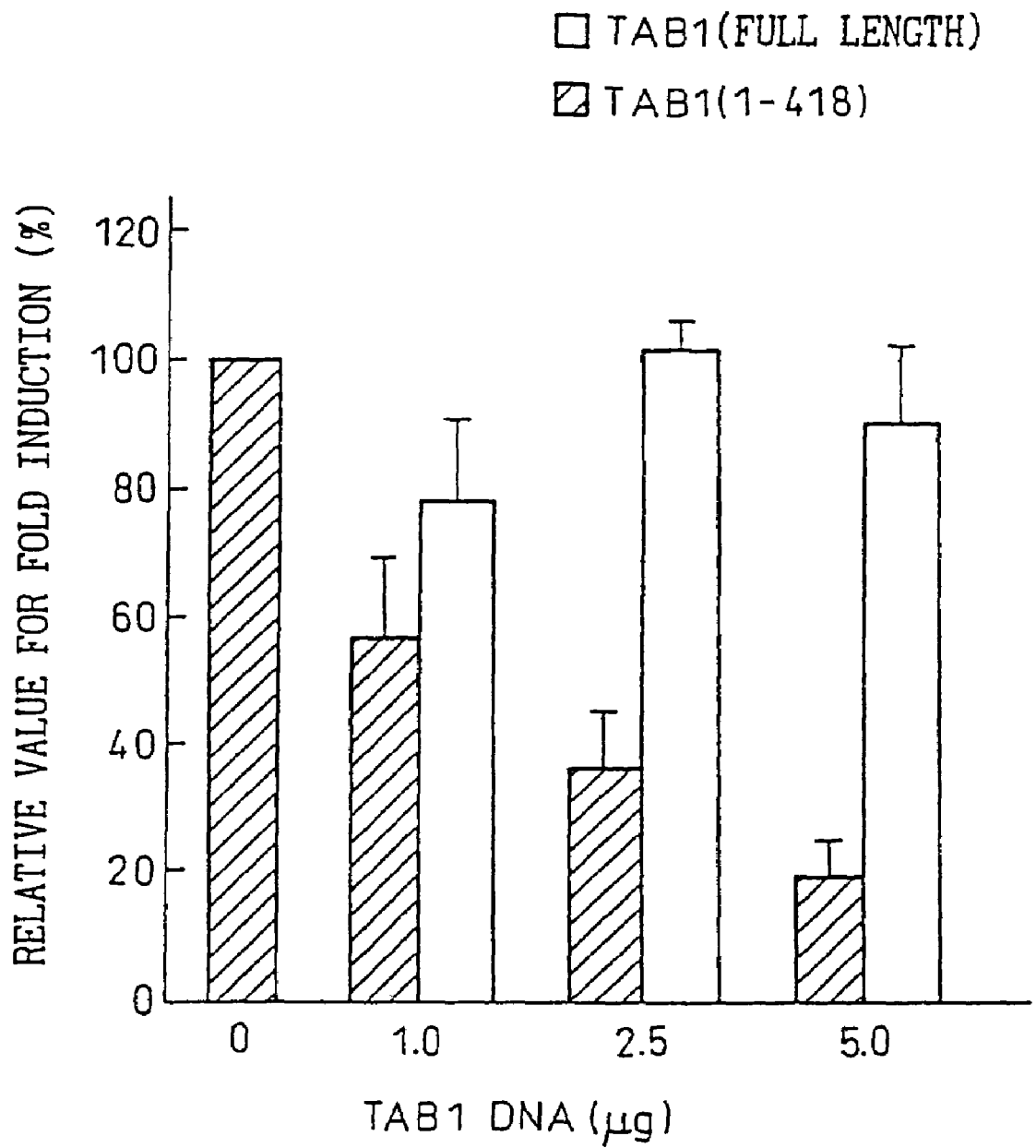

TAB1 PROTEIN AND DNA CODING THEREFORE

BACKGROUND OF INVENTION

1. Field of Invention

The present invention relates to TAB1 protein which forms a part of the signal-transduction pathway of Transforming Growth Factor-β (TGFβ), and to a gene coding therefor.

2. Related Art

TGF-β is a multifunctional factor which regulates various cellular functions. As one of those functions, TGF-β is responsible for the repair and reproduction of tissues with various types of injury.

Abnormal production of TGF-β in cases of chronic injury sometimes results in an imbalance between the repair and the reproduction of tissues and thus pathological fibrosis. Hepatic fibrosis is known as one condition resulting from an imbalance in TGF-β production. In the liver, TGF-β accelerates production of extracellular matrix proteins which are responsible for fibrosis, while inhibiting synthesis of extracellular matrix protein catabolic enzymes and inducing catabolic enzyme inhibitors, and it thus acts as a major causative factor of hepatic fibrosis.

One of known members of signal-transduction pathway belonging to the TGF-β superfamily is the Mitogen-Activated Protein Kinase Kinase Kinase (MAPKKK) system.

The MAPK pathway is a conserved eukaryotic signal-transduction pathway which converts receptor signals into various functions, and the system comprises 3 different protein kinases, specifically MAPKKK mentioned above, MAPKK and MAPK, with MAPK being activated through phosphorylation by MAPKK, and MAPKK in turn being activated by MAPKKK (E. Nishida et al., Trends Biochem. Sci. Vol. 18, p. 128 (1993); K. J. Blumer et al, op. cit. Vol. 19, p. 236 (1994); R. J. David, op. cit. Vol. 19, p. 470 (1994); C. J. Marchall, Cell, Vol. 80, p. 179 (1995)).

TAK1, which is a member of the MAPKKK family which functions in signal-transduction pathways belonging to the TGF-β superfamily, has been identified by K. Yamaguchi (K. Yamaguchi et al., Science, Vol. 270, p. 2008 (1995)).

TGF-β transduces signal through a heteromeric complex of type I and type II TGF-β receptors, which are transmembrane proteins comprising cytoplasmic serine- and threonine-specific kinase domains (J. L. Wrana et al., Nature, Vol. 370, p. 341 (1994); D. M. Kingsley et al.,. Genes Dev., Vol. 8, p. 133 (1994)). However, little is known at the molecular level about the signal-transduction mechanism downstream from the TGF-β receptors.

SUMMARY OF INVENTION

It is an object of the present invention, therefore, to provide TAB1 protein which is a newly discovered member in the TGF-β receptor signal-transduction pathway, and to a gene coding therefor. The present invention further provides a screening method for TGF-β signal-transduction pathway inhibitors. TAB1 refers to a protein which binds to TAK1 (TAK1 Binding protein).

In order to achieve these objects, the present invention provides TAB1 protein having the amino acid sequence shown in SEQ ID NO: 1; a protein having an amino acid sequence shown in SEQ ID NO: 1 modified by substitution, deletion and/or addition of one or more amino acids in the amino acid sequence shown in SEQ ID NO: 1, and having a biological property of TAB1 protein; a protein wherein the 52nd amino acid of the amino acid sequence shown in SEQ ID NO: 1 is arginine; a protein encoded by DNA which can hybridize with DNA having the nucleotide sequence shown in SEQ ID NO: 7 under hybridization conditions of 60° C., 0.1×SSC, 0.1% sodium dodecyl sulfate, and which has a biological property of TAB1 protein; a protein having an amino acid sequence consisting of amino acids from amino acid positions 21 to 579 of the amino acid sequence shown in SEQ ID NO: 1; and a polypeptide having the amino acid sequence consisting of the 68 amino acids from amino acid positions 437 to 504 of the amino acid sequence shown in SEQ ID NO: 1.

The present invention further provides a method for producing any of the above-mentioned proteins or polypeptides comprising the steps of culturing a host transformed by an expression vector comprising DNA encoding the protein or polypeptide, and recovering the protein or polypeptide from the culture.

The present invention still further provides a method for inducing mammalian cells to produce any of the above-mentioned proteins or polypeptides comprising the step of introducing DNA encoding the protein or polypeptide into mammalian cells.

The present invention still further provides DNA encoding any of the above-mentioned proteins or polypeptides, an expression vector comprising the DNA, and a host transformed by the expression vector.

The present invention still further provides a method for screening TGF-β signal-transduction pathway inhibitors.

BRIEF DESCRIPTION OF THE DRAWINGS

FIG. 4 shows the amino acid sequence of TAB1 (SEQ ID NO: 1) with an insertion of partial TAK1 sequence (SEQ ID NO: 8) for comparison.

FIG. 6 is an immunoblot diagram showing association of TAB1 and TAK1 in mammalian cells.

FIG. 8 is a graph showing enhanced expression of a luciferase reporter gene by the copresence of TAK1 and TAB1 in mammalian cells stimulated by TGF-β.

FIG. 9 is a graph showing inhibition of the TGF-β-induced luciferase reporter gene expression by TAB-lacking the C-terminus (TAB1 (1-418)).

DETAILED DESCRIPTION

Figure 1:
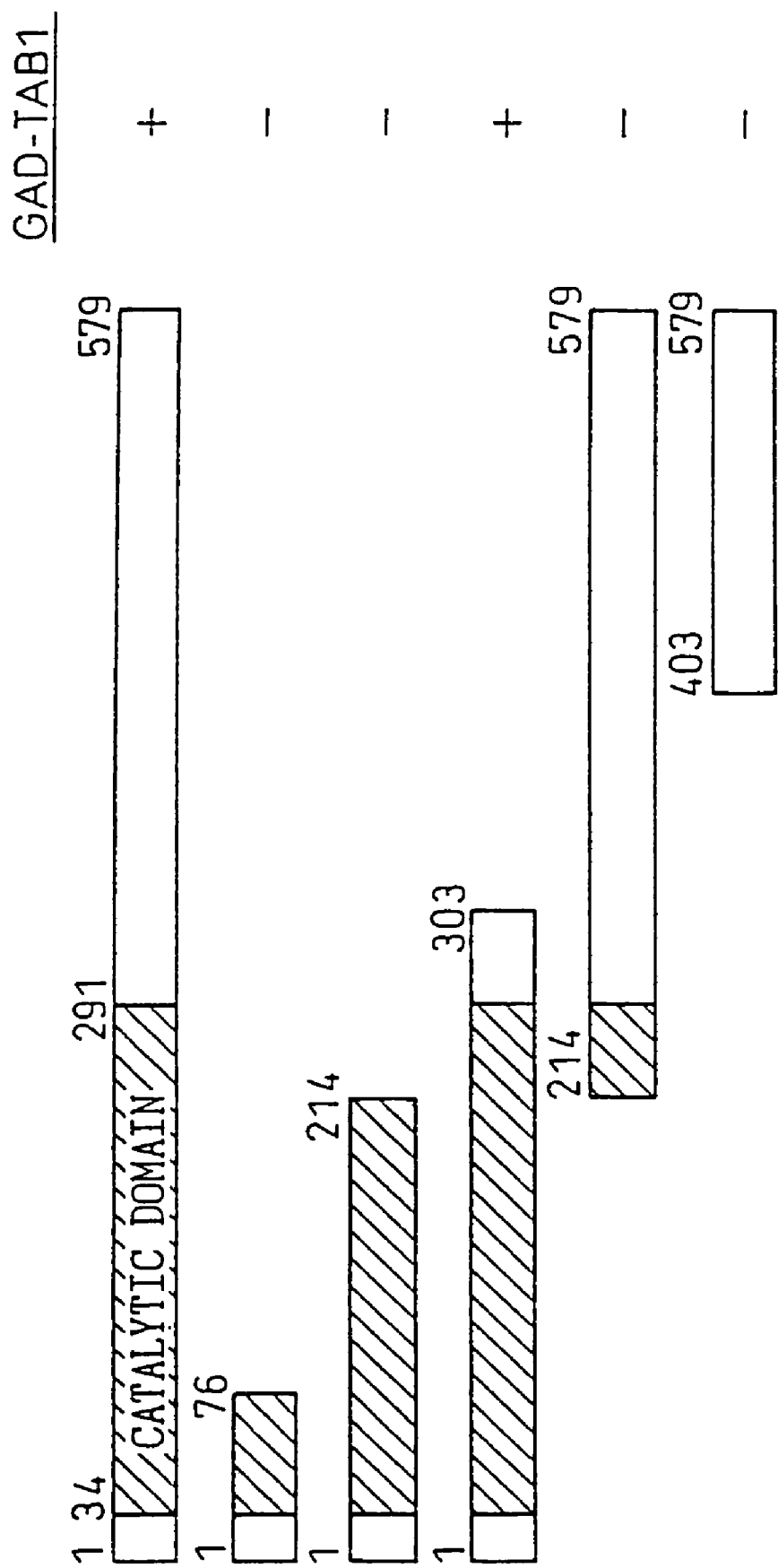
FIG. 1 shows the regions on the TAK1 protein to which TAB1 protein binds. The shaded areas indicate the TAK1 catalytic domain.

The TAB1 protein according to the invention has the characteristic of activating TAK1 by binding TAK1 in the signal-transduction pathway of transforming growth factor-β(TGF-β). This and other characteristics are described in detail Examples 2 to 4 and 6 to 10.

The TAB1 protein of the invention has the amino acid sequence (SEQ ID NO: 1) derived from the nucleotide sequence of cDNA cloned by the method described in Examples 1 and 5. However, it is well known that proteins with biological activity exist whose amino acid sequences have been modified by a substitution, deletion and/or addition of one or more amino acids, and which maintain a biological property of the wild protein. Thus, the present invention encompasses proteins having an amino acid sequence modified by a substitution, deletion and/or addition of one or more amino acids in the amino acid sequence shown in SEQ ID NO: 1, and having a biological property of TAB1 protein.

One embodiment thereof is a protein wherein the 52nd amino acid of the amino acid sequence shown in SEQ ID NO: 1 is arginine.

It is also known that once DNA coding for a specific protein has been cloned, the DNA may be used as a probe for screening of a DNA library from organs or tissue different from the organs or tissue from which the protein was obtained, or a DNA library from another species, to obtain DNA coding for a protein with similar biological property though having a different amino acid sequence. Thus, the present invention also encompasses proteins encoded by DNA which can hybridize with DNA having the nucleotide sequence shown in SEQ ID NO: 7 under hybridization conditions of 60° C., 0.1×SSC, 0.1% sodium dodecyl sulfate, and which has a biological property of TAB1 protein.

An example of a modified protein according to the invention is a protein having an amino acid sequence consisting of amino acids from amino acid positions 21 to 579 of the amino acid sequence shown in SEQ ID NO: 1. This protein has the biological property of TAB1 protein. An instance of a modified polypeptide according to the invention is a polypeptide having the amino acid sequence consisting of the 68 amino acids from amino acid positions 437 to 504 of the amino acid sequence shown in SEQ ID NO: 1. This polypeptide has the properties of activating TAK1 kinase activity upon binding to TAK1.

Another example of a modified protein according to the invention is a fused protein between the aforementioned protein or polypeptide and another protein, which has a biological activity of TAB1.

Proteins or polypeptides of the invention can imitate the actual physiological function of TGF-β by, for example, activating TAK1 which is important to the TGF-β signal-transduction pathway, as well as inhibit binding between TAK1 and TAB1 by their binding to TAK1, and they are therefore useful for methods of screening substances which act as agonists or antagonists against cell growth suppression, immunosuppression and bone differentiation.

DNA coding for a protein of the invention is, for example, DNA coding for the amino acid sequence shown in SEQ ID NO: 1. Such DNA may be obtained, for example, by the method described in Examples 1 and 5, and it has the nucleotide sequence shown in SEQ ID NO: 7. However, DNA coding for the amino acid sequence shown in SEQ ID NO: 1 does not necessarily have the nucleotide sequence shown in SEQ ID NO: 7, as it may consist of other codons coding for the same amino acids. For example, the human derived nucleotide sequence shown in SEQ ID NO: 7 may be altered to include a codon which is efficiently translated in such microorganisms as bacteria or yeast, and this may be accomplished using a well-known technique such as site-specific mutagenesis with a primer.

DNA according to the invention coding for a protein or polypeptide having an amino acid sequence modified by a substitution, deletion and/or addition of one or more amino acids in the amino acid sequence shown in SEQ ID NO: 1 may be prepared by a well-known method such as site-specific mutagenesis or the PCR, using DNA with the nucleotide sequence shown in SEQ ID NO: 7 as the template. Alternatively, DNA coding for a protein or polypeptide wherein the modified amino acid sequence is shorter than the natural protein may be obtained, for example, by introducing a translation initiation codon and/or translation termination codon into naturally occurring DNA, such as cDNA. The introduction of these codons may be accomplished by site-specific mutagenesis or the PCR. Alternatively, it may be achieved by cleaving the natural DNA, such as cDNA, with an appropriate restriction enzyme, and adding the desired oligonucleotide if necessary.

DNA which can be hybridized with DNA having the nucleotide sequence shown in SEQ ID NO: 7 of the invention and which codes for a protein having a biological property of TAB1 may be obtained by screening a genomic DNA library or cDNA library prepared, for example, from the various tissues and organs mentioned in Example 6, including the heart, brain, placenta, liver, skeletal muscle, kidney, pancreas, spleen, thymus, prostate, testicles, ovaries, small intestine, colon, peripheral leukocytes, etc., using the nucleotide sequence shown in SEQ ID NO: 7 of the invention or a portion thereof as the probe. The DNA library is not limited to a human derived one, and may be derived from other animals such as rats, mice, rabbits, goats, sheep, cattle or pigs.

The present invention also relates to an expression vector comprising an aforementioned DNA and to a host transformed therewith. The expression vector will differ depending on the host. The host cells used according to the invention may be from any prokaryotic or eukaryotic organisms. The prokaryotic organisms used may be bacteria, for example, microorganisms belonging to the genus *Escherichia* such as *Escherichia coli*, microorganisms belonging to the genus *Bacillus* such as *Bacillus subtilis*, etc., and the eukaryotic organisms may be lower eukaryotic organisms, such as filamentous fungi and yeast.

Filamentous fungi include microorganisms belonging to the genus *Aspergillus* such as *Aspergillus niger* and *Aspergillus orizae* and microorganisms belonging to the genus *Penicillium*, while the yeast may be microorganisms belonging to the genus *Saccharomyces* such as *Saccharomyces cerevisiae*.

Higher eukaryotic organisms which may be used include various animal and plant cells, for example, immortralized cultured animal cells such as COS cells, CHO cells and NIH3T3, etc. Insect cells such as Sf9, Sf12, etc. may also be used.

The expression vector of the invention includes, in addition to DNA coding for a protein or polypeptide of the invention, expression regulating sequences, such as promoters, which are functionable in the host.

Promoters for bacteria, for example *E. coli*, include T3 and T7, while promoters for yeast include glycolytic enzyme gene promoters such as GAL1 promoter and GAL4 promoter. The promoter for animal cells may be a viral promoter, such as CMV promoter or SV40 promoter.

The transformation of the host by an expression vector, culturing the host, and the collection and purification of the protein or polypeptide of the invention from the culture may be accomplished according to conventional methods. For example, the isolation and purification of the protein or polypeptide from the culture may be accomplished using any conventional means for isolating and purifying proteins and polypeptides, such as ammonium sulfate precipitation, gel filtration or reverse phase HPLC, either alone or in combinations.

The present invention also relates to a screening method for TGF-β signal-transduction pathway inhibitors. A sample containing TGF-β signal-transduction pathway inhibitors is brought to contact with or introduced into cells expressing a protein with a biological activity TAB1 and TAK1 (K. Yamaguchi et al., Science, Vol. 270, p. 2008 (1995)), and the TAK1 activity is then measured. The protein or polypeptide with biological activity of TAB1 and TAK1 may also be fused with another protein, and the cells expressing them may be yeast cells or mammalian cells. This screening system may be constructed according to the method described in Examples 1, 2, 3, 4, 7, 8 and 9.

The sample containing TGF-β signal-transduction pathway inhibitors is brought to contact with or introduced into the constructed screening system, and the TAK1 kinase activity is measured. The method for measuring the TAK1 kinase activity may be measurement of the kinase activity of TAK1 itself, or measurement of the kinase activity of MAPKK or MAPK which are downstream from TAK1 in the signal-transduction pathway and are activated by TAK1. The activity of a target gene in the MAPK pathway or a reporter gene under the control of the target gene promoter may also be measured based on the amount of mRNA or expressed form of the gene.

The screening method for TGF-β signal-transduction pathway inhibitors according to the invention allows screening of substances which inhibit binding between TAB1 and TAK1 and can thus serve as a means of therapy for diseases involving abnormal-production of TGF-β.

EXAMPLES

The present invention will now be explained in more detail by way of the following examples.

Example 1

Analysis of the TAK1-dependent pathway functioning for TGF-β signal-transduction was made using a yeast 2-hybrid system (S. Frelds et al., Trend Genet. 10, 286 (1994)), and a protein having direct interaction with TAK1 was sought.

First, an expression vector was constructed by linking the TAK1 gene and a gene coding for the LexA DNA-binding domain. pLexA-TAK1Δ contains the TAK1ΔN coding sequence (K. Yamaguchi et-al., Science, Vol. 270, p. 2008 (1995)) inserted in frame into pBTM116 (A. B. Vojtek et al., Cell, Vol. 74, p. 205 (1993)). A yeast 2-hybrid system was used to identify a protein encoded in a human brain cDNA library and interacting with TAK1ΔN.

The two hybrids were expressed in *Saccharomyces cerevisiae* L40 (LYS2:LexA-HIS3) containing an integrated reporter construct with a binding site for LexA protein located upstream from the yeast HIS3 coding region. Interaction between the two hybrid proteins causes transactivation of the reporter construct, allowing growth of the yeast in the absence of histidine (SC-His).

The LexA-TAK1ΔN fused protein alone confers expression of HIS3 in a sufficient amount to allow growth without requiring exogenous histidine. However, histidine auxotrophy can be achieved by growing the cells in the presence of 40 mm 3-aminotriazole (3-AT) which is a chemical inhibitor of the HIS3 gene product imidazole glycerol dehydrogenase (G. M. Kishore et al., Annu. Rev. Biochem. Vol. 57, p. 627 (1988)).

Yeast was transformed using a bait plasmid together with a fish plasmid containing the human brain cDNA expression library clone linked to the gene coding for the GAL4 activating domain (GAD). A positive clone of TAB1 cDNA coding for the protein was obtained from about $1 \times 10^6$ transformants. The GAD fused protein expressed by this isolated DNA will hereinafter be referred to as GAD-TAB 1.

Example 2

A series of LexA-TAK1 deletion chimera were tested by the 2-hybrid method to determine the site in TAK1 which is responsible for interaction with TAB1. An expression vector coding for the full TAK-1 or deletion construct thereof fused to the LexA DNA-binding domain was used for simultaneous transformation of the yeast reporter strain L40 together with pGAD-TAB1. The DNA coding for each of the TAK1 deletion constructs was prepared from DNA coding for the full TAK1.

The aforementioned plasmid pGAD-TAB1 was obtained by cloning TAB1 cDNA at the EcoRI site of pBS (W. O. Bullock et al., Biotechniques, Vol. 5, p. 376 (1987)). The interaction between the fused proteins expressed by this plasmid is indicated by the ability of the yeast strain, to grow on a plate of SC—HIS medium containing 40 mM 3-AT. The results are shown in FIG. 1. The right side of this graph indicates whether TAK1 or its deletion form interacted with TAB1 (+) or not (−). These results demonstrate that TAB1 interacts with the N-terminal domain of TAK1.

Example 3

A protein interacting with TAK1 may contain both the upstream control region and the downstream target. If TAB1 plays a role in activation of TAK1, then their simultaneous expression would be expected to influence activity of TAK1 in yeast. The present inventors have disclosed a system for assaying mammalian MAPKKK activity in a yeast pheromone-induced MAPK pathway (K. Yamaguchi et al., Science, Vol. 270, p. 2008 (1995); K. Irie et al., Science, Vol. 265, p. 1716 (1994)). An activated form of TAK1 (TAK1ΔN) can substitute for Ste11 MAPKKK activity.

Specifically, the pheromone-activated MAPK pathway consists of Ste11, Ste7, and Fus3 or Kss1 kinases, which correspond to MAPKKK, MAPKK and MAPK, respectively. These yeast protein kinases act sequentially to transduce signals to the transcription factor Ste12, upon which Ste12 in turn activates transcription of mating-specific genes such as FUS1 (I. Herskowitz, Cell, Vol. 80, p. 187 (1995); D. E. Levin et al., Curr. Opin. Cell Biol., Vol. 7, p. 197 (1995); J. Schultz et al., Jr. Curr. Opin. Gene Dev., No. 5, p. 31 (1995)).

The FUS1p::HIS3 reporter gene comprises the FUS1 upstream activating sequence linked to the HIS3 open reading frame, and signal activity of the his3ΔFUS1p::HIS3 strain may be monitored by the ability of cells to grow on SC-His medium (His⁻ phenotype).

Strain his3Δste11ΔFUS1p::HIS3STE7$^{P368}$ (proline substitution at serine-368) has a His⁻ phenotype (K. Irie et al., Science, Vol. 265, p. 1716 (1994)).

Expression of TAK1ΔN in this strain confers a His⁺ phenotype (K. Yamaguchi et al., Science, Vol. 270, p. 2008 (1995)). Thus, the activated form of TAK1 may substitute for Ste11 activity in an Ste7$^{P368}$-dependent manner. However, expression of the full-length TAK1 does not complement the ste11Δ mutation, suggesting that the yeast does not have the putative activating factor for TAK1 (K. Yamaguchi et al., Science, Vol. 270, p. 2008 (1.995)).

The GAD-TAB1 constructs were tested for their ability to complement the ste11Δ mutation in the presence of TAK1, using the yeast MAPK pathway. Specifically, yeast strain SY1984-P (his3Δste11ΔFUS1p::HIS3STE7$^{P368}$) was transformed with pNV11-HU11 (TAK1ΔN)+pGAD10 (GAD) (Clontech), pNV11-HU11F (TAK1)+pGAD10, pNV11-HU11F+pGAD-TAB1 or pNV11+pGAD-TAB, and the transformants were folded onto an SC-His plate and incubated at 30° C.

The aforementioned strain SY1984-P is SY1984 (his3Δste11ΔFUS1p::HIS3) transformed by plasmid pNC318-p368 containing STE7$^{P368}$ under the control of CYC1 promoter (K. Irie et al., Science, Vol. 265, p. 1716 (1994)). The aforementioned plasmids pNV11-HU11 and pNV11-HU11F respectively express the shortened TAK1ΔN (amino acids 21-579) and the full-length TAK1-under the control of TDH3 promoter (K. Yamaguchi et al, Science, Vol. 270, p. 2008 (1995)).

Figure 2:
FIG. 2 shows complementation of the Ste11 deletion by the copresence of TAK1 and TAB1 in an Ste11 deletion strain, in the pheromone-activated MAPK pathway of yeast.

The results are shown in FIG. 2. The left panel indicates whether the yeast strain tested expressed TAK1ΔN or TAK1, and whether GAD-TAB1 was simultaneously expressed or not. The right panel shows the growth of the cells on the SC-His plate. Each of the patches represents the results for an independent transformant.

The GAD-TAB1 and TAK1 simultaneous transformant restored the effect of the Ste11 deletion. This indicates that TAB1 reinforces the function of TAK1.

Example 4

In order to determine whether TAK1 activity is increased in TAB1-expressing yeast, an expression DNA vector containing TAK1 carrying the hemagglutinin (HA)-derived C-terminal epitope and a catalytically inactive TAK1 mutant [TAK1-K63W wherein lysine at position 63 of the ATP-binding site is replaced with tryptophan (K. Yamaguchi et al., Science, Vol. 270, p. 2008 (1995)] was used to transform yeast cells in the absence and in the presence of the TAB1 gene.

The DNA sequence coding for an epitope recognized by the HA-specific monoclonal antibody 12CA5 was joined in frame with the TAK1-coding sequence and TAK1-K63W C-terminus by the polymerase chain reaction (PCR). All of the constructs were expressed by TDH promoter. The TAB1 expression plasmid pGAP-HTH9M expresses 68 C-terminal amino acids. YEpGAP112 is a multicopy plasmid TRP1 containing TDH3 promoter [H. Banno et al., Mol. Cell Biol. 13, 475 (1993)].

A sequence coding for the 68 C-terminal amino acids of TAB1 was amplified by the PCR using the 5' primer: 5'-GAGAATTCATGCGGCAAAGC-3' (SEQ ID NO: 2) containing the EcoRI site and ATG codon and the 3'-primer: 5'-GGGTCGACTACGGTGC-3' (SEQ NO: 3) containing the SalI site. A 240 bp EcoRI-SalI fragment produced by PCR was inserted into the EcoRI-SalI gap of YEpGAP112 to construct pGAD-HTH9M.

Figure 3:
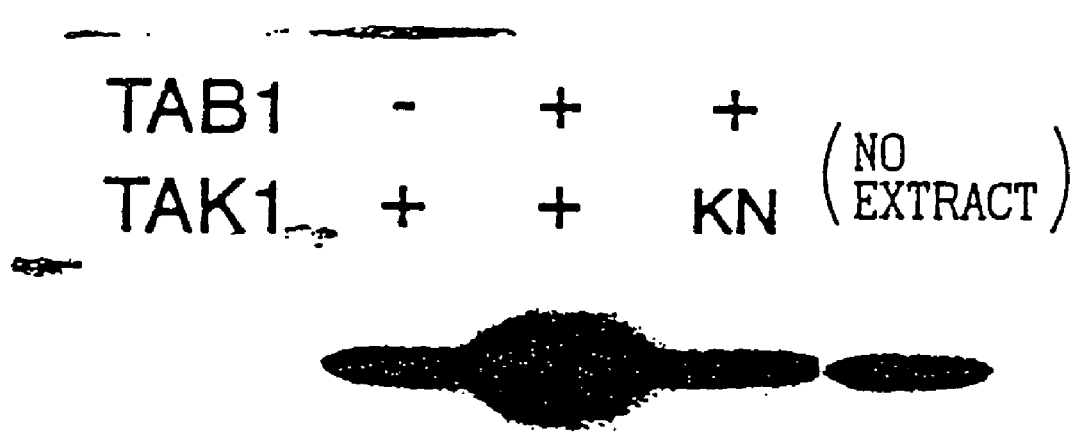
FIG. 3 is the results of electrophoresis shown in a photographs showing the results of the in vitro experiment indicating reinforcement of TAK1 activity by TAB1.

The results are shown in FIG. 3. As described above, yeast strain SY1984 was transformed with the aforementioned plasmid coding for TAK1-HA and plasmid coding for TAK1-K63W, and the empty vector YEpGAP112(-) or pGAP-HTH9M(+) coding for TAB1 was additionally inserted into the transformant. TAK1-HA(-) or TAK1-K63W-HA(KN) was immunoprecipitated from each of the cell extracts and the immunoprecipitates were subjected to in vitro kinase assays. Specifically, 60 ml of yeast cell culture was allowed to grow to an optical density of 0.8 at 600 nm, and a cell extract was prepared with a cytolytic buffer solution (K. Irie et al., Science, Vol. 265, p. 1716 (1994)) and then separated by centrifugation at 100,000 g for 30 minutes.

The supernatant was subjected to immunoprecipitation with an antibody against HA. That is, a portion (300 μl) of the supernatant was mixed with 2 μl of antibody and 90 μl of Protein A-Sepharose, and the immunocomplex was washed 3 times with a cytolytic buffer solution and used for the kinase assay (K. Yamaguchi et al., Science, Vol. 270, p. 2008 (1995)). Immunoblot analysis of each immunoprecipitate with the HA-specific monoclonal antibody 12CA5 demonstrated that approximately the same amount of TAK1-HA or TAK1-K63W-HA was recovered in each sample. This suggests that expression of TAB1 does not affect the amount of TAK1 expression.

The immunoprecipitated TAK1 was assayed based on the ability to activate recombinant XMEK2 (SEK1), with the recombinant XMEK2 (SEK1) activity being assayed based on its ability to phosphorylate catalytically inactive (KN)p38 (MPK2) (K. Yamaguchi et al., Science, No. 270, p. 2008 (1995)). After electrophoresis, phosphorylation of KN-p38 (MPK2) was detected by autoradiography. No extract exhibited a kinase assay value without the enzyme extract. This level corresponds to the XMEK2 basal activity. The experiment was conducted at least 3 times, giving the same results each time.

The results are shown in FIG. 3. The results of kinase assay for TAK1-HA and TAK1-K36W-TAK1 indicate that TAB1 increases TAK1 kinase activity. The activity increase was not observed for immunocomplexes from cells expressing TAK1-K63WKN and TAB1, indicating that the observed kinase activity was attributable to TAK1. These results demonstrate that TAB1 activates TAK1 kinase activity by directly binding to the catalytic domain of TAK1.

Example 5

To obtain the full-length coding sequence for TAB1, a human kidney library was screened using as a probe the aforementioned partial sequence of TAB1 cDNA obtained from the yeast 2-hybrid system. Two independent clones carried 3.1 kb cDNA containing a single open reading frame (ORF) starting from the initial methionine codon matching the Kozak consensus. The 5'-terminus was identified by the 5' RACE method using 5'-RACE-Ready cDNA (Clontech).

The proposed N-terminal nucleotide sequence of the coding sequence (CC<u>AA</u><u>ATG</u>G) corresponds to the Kozak consensus (M. Kozak, J. Cell Biol. Vol. 108, p. 229 (1989)), and the ATG codon is not present before it.

The TAB1 nucleotide sequence was determined by the dideoxynucleotide chain termination method. An amino acid sequence was deduced from the nucleotide sequence of the full-length TAB1 cDNA. As a result, two different clones were obtained with cytosine and adenine as the 185th nucleotide, respectively. The clone with cytosine as the 185th nucleotide encodes for serine as the 52nd amino acid, and the clone with adenine as the 185th nucleotide encodes arginine as the 52nd amino acid.

The nucleotide sequence of the clone with cytosine as the 185th nucleotide is shown in SEQ NO: 7, and its amino acid sequence is shown in FIG. 4 and in SEQ ID NO: 1. The nucleotide sequence of the clone with adenine as the 185th nucleotide is shown in SEQ ID NO: 6, and its amino acid sequence is also shown in SEQ ID NO: 4.

The cDNA of the clone with cytosine as the 185th nucleotide was subcloned at the EcoRI and SmaI sites of pBS to prepare plasmid TABI-f-4, while the cDNA of the clone with adenine as the 185th nucleotide was subcloned at the EcoRI site of pBS to prepare plasmid pBS-TAB1. *E. coli* containing plasmid pBS-TAB1 was named *Escherichia coli* HB101 (pBS-TAB1) and was deposited at the National Institute of Bioscience and Human Technology Agency of Industrial Science and Technology on Apr. 19, 1996 as FERM BP-5508. *E. coli* containing plasmid TABI-f-4 was named *Escherichia coli* DH5α (TABI-f-4) and was deposited at the National Institute of Bioscience and Human Technology Agency of Industrial Science and Technology on Jul. 19, 1996 as FERM BP-5599.

The following experiment was conducted using the clone having the nucleotide sequence shown in SEQ ID NO: 7.

In FIG. 4, A=Ala, C=Cys, D=Asp, E=Glu, F=Phe, G=Gly, H=His, I=Ile, K=Lys, L=Leu, M=Met, N=Asn, P=Pro, Q=Gln, R=Arg, S=Ser, T=Thr, V=Val, W=Trp and Y=Tyr. The 68 C-terminal amino acids of GAD-TAB1 isolated using the yeast 2-hybrid system are boxed.

The N-terminal sequence of TAK1 is aligned to show the region with similarity to the same segment of TAK1. The identical and conserved amino acids with respect to those of TAK1 are marked with asterisks and dots, respectively.

The ORF suggested a protein of 504 amino acids having a molecular size of 55 kDa, without clear similarity to any known protein and without any motif indicating biological function.

Example 6

Figure 5:
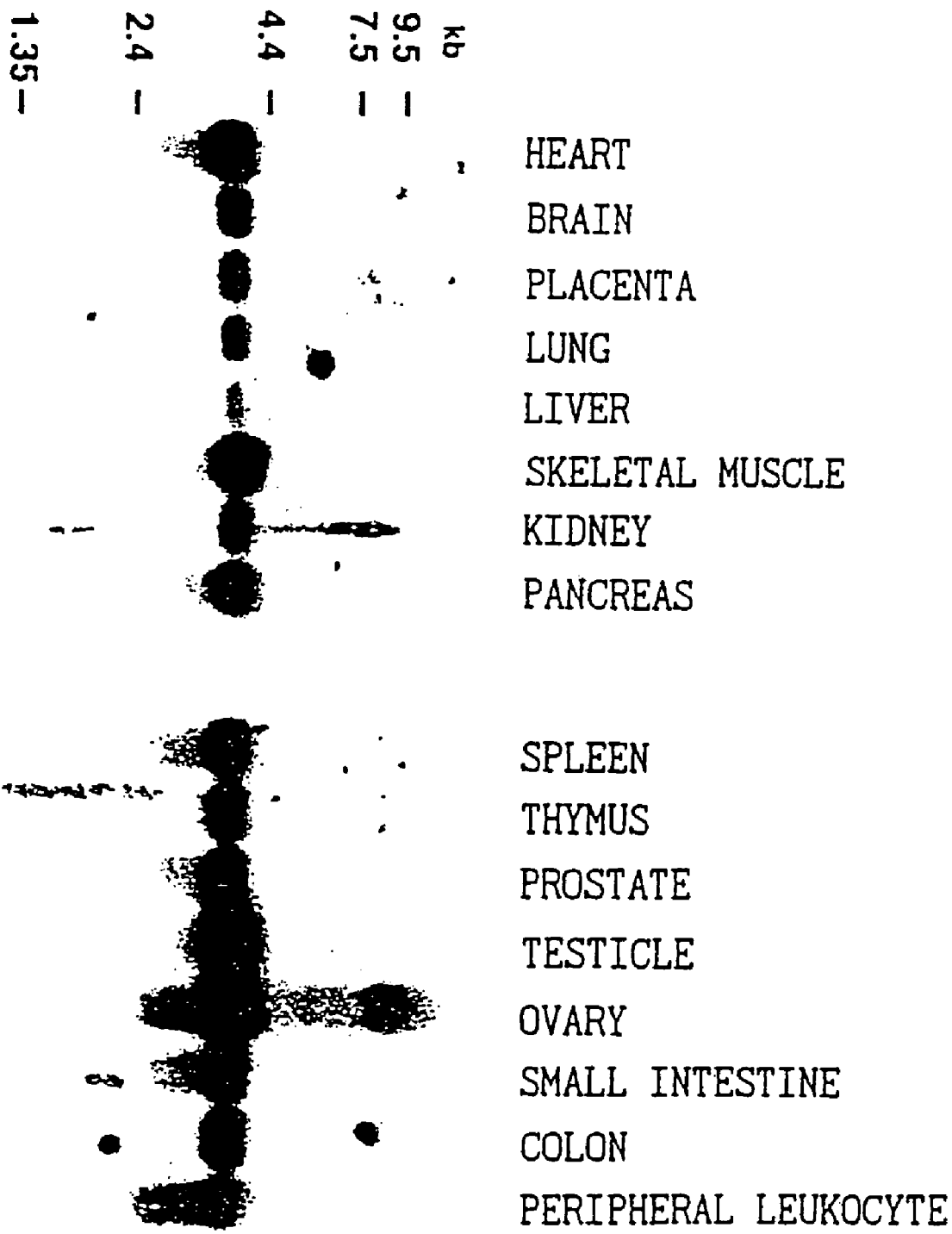
FIG. 5 is an electrophoresis diagram showing expression of mRNA coding for TAB1 in various organs and tissues.

The expression patterns of TAB1 mRNA in different human cells were analyzed by Northern blotting. Human tissue blots (Clontech) of mRNA isolated from 16 tissues were probed with $^{32}$P-labelled TAB1 cDNA, and subjected to autoradiography. The results are shown in FIG. 5. Each of the lanes contained 2 μg of mRNA. The probe was labelled with [α-$^{32}$P]-dCTP using a Multiprime Labeling Kit (Amersham), and hybridized as described by H. Shibuya et al.,. Nature, Vol. 357, p. 700 (1992). A major transcription product of about 3.5 kb was detected in all of the tissues tested.

Example 7

In order to confirm association of TAB1 and TAK1 in mammalian cells, an expression vector producing HA epitope-labelled TAK1 (HA-TAK1) (K. Yamaguchi et al., Science, Vol. 270, p. 2008 (1995)) and an expression vector producing Myc epitope-labelled TAB1 (Myc-TAB1) were used for transient transfection of MC3T3-E1 murine osteoblasts (S. Ohta et al., FEBS Lett., Vol. 314, p. 356 (1992)). The latter plasmid was obtained in the following manner.

The full-length TAB1 cDNA was subcloned in pCS2MT vector containing 6 copies of the Myc epitope (LEQKLI-SEEDLN (SEQ ID NO: 5)) (single letter amino acid sequence notation) recognized by the Myc-specific monoclonal antibody 9E10 (D. L. Tumer et al., Genes Dev., Vol. 8, p. 1434 (1994)). In the plasmid thus obtained, pCS2MT•TAB1, the Myc epitope tag is linked in frame with the DNA sequence corresponding to the N-terminus of TAB1. pCSA2MT-TAB1 was digested with BamHI and XbaI. The fragment was isolated and inserted at the EcoRI-XbaI site of the mammalian expression vector pEF. This plasmid causes expression of TAB1 from the human elongation factor 1α (EF1α) promoter.

The cell extract was subjected to immunoprecipitation with the HA-specific monoclonal antibody 12CA5 (lane 2 in FIG. 6), the Myc-specific monoclonal antibody 9E10 (lane 3 in FIG. 6) or a control nonimmune IgG (lane 4 in FIG. 6). The immunocomplex was washed and separated by SDS-PAGE, and then transferred to nitrocellulose for immunoblotting using the Myc-specific antibody (top lanes of FIG. 6) and HA-specific antibody (bottom lanes of FIG. 6).

The cell extracts were then immediately subjected to immunoblot analysis (lane 1 of FIG. 6). As FIG. 6 shows, a considerable amount of Myc-TAB1 was detected in each immunoprecipitation, indicating that TAK1 can be immunoprecipitated with TAB1. A reciprocal experiment blotting the immunoprecipitated protein with the HA-specific antibody confirmed association of TAB1 and TAK1. These experiments indicate that TAB1 can associate with TAK1 in mammalian cells as in yeast.

Example 8

It was investigated whether overexpression of TAB1 can activate TAK1 kinase activity. MC3T3-E1 cells were transiently transfected with HA-TAK1 in the presence of (+) and in the absence of (−) Myc-TAB1. The cells were treated (+) or untreated (−) with 20 ng/ml TGF-β1 for 10 minutes and then HA-TAK1 was immunoprecipitated in the manner described in Example 3, after which the kinase activity was assayed. Specifically, a portion of the immunoprecipitate was immunoblotted with HA-specific antibody. The results are shown in FIG. 7.

Figure 7:
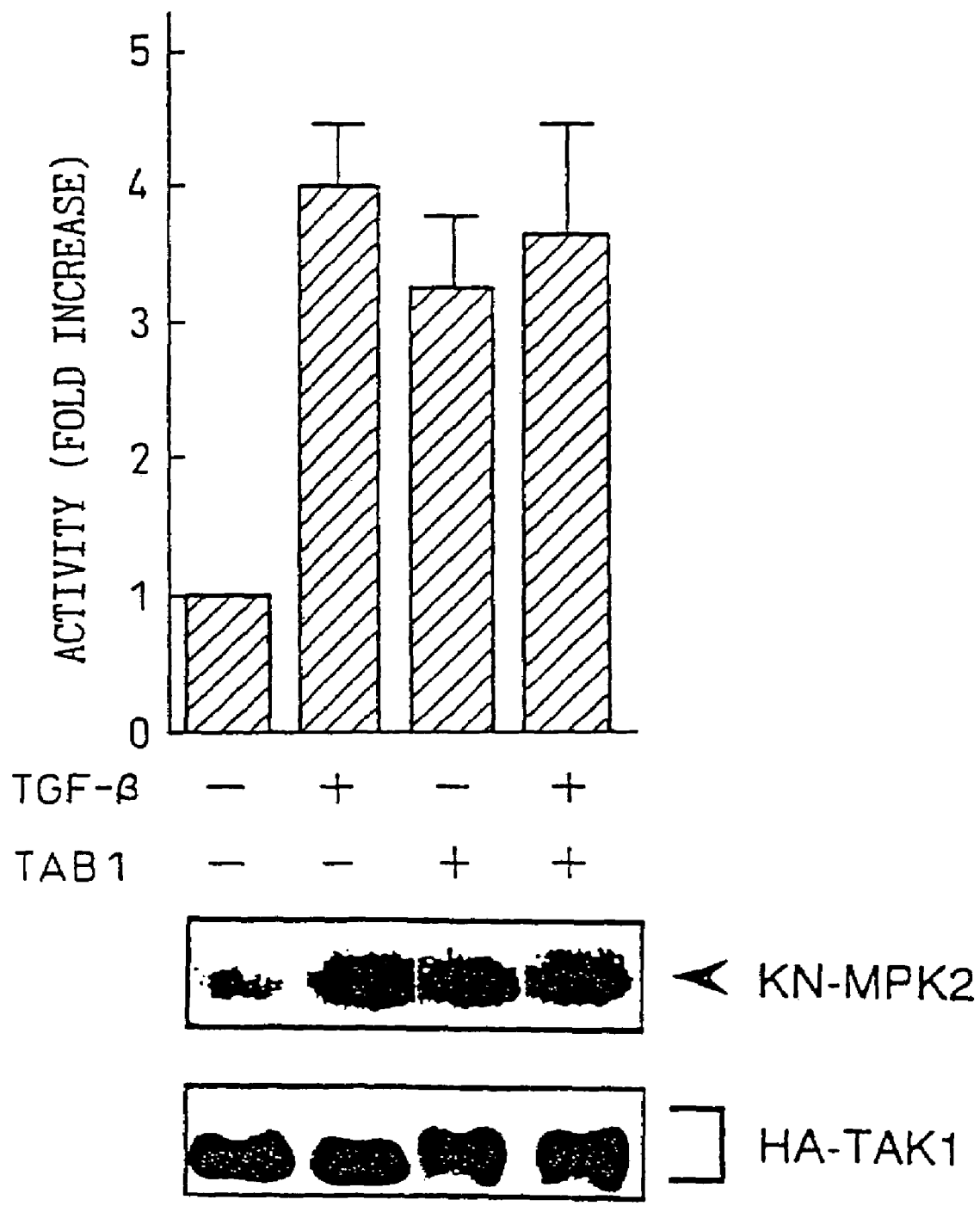
FIG. 7 contains a graph showing enhancement of TAK1 kinase activity by TAB1 in mammalian cells (top), and a blot diagram showing comparable amounts of production of TAK1 and KN-MPK2.

The activity is given as a fold increase relative to the amount of HA-TAK1 from unstimulated cells, and is expressed as mean±SEM from at least 3 experiments (top graph in FIG. 7). HA-TAK1 did not directly phosphorylate KH-p38(MPK2) (K. Yamaguchi et al., Science, Vol. 270, p. 2008 (1995)). The middle panel is the autoradiogram showing phosphotylation of KN-p38(MPK2). The lower panel shows immunoblot analysis of each of the immunoprecipitates with the HA-specific monoclonal antibody 12CA5, where it is seen that approximately the same amount of TAK-HA was recovered in each sample. The data shown in the middle and lower panels are from typical experiments.

The in vitro assay of the TAK1 immunoprecipitation suggests that TAK1 activity was stimulated in cells transfected with TAB1 even in the absence of TGF-β. Activation of TAK1 by overexpression of TAB1 was comparable to the activation observed in cells stimulated with TGF-β which expressed only HA-TAK1.

Example 9

TGF-β causes rapid increase in the amount of mRNA coding for plasminogen activating factor inhibitor-1 (PAI-1) (M. R. Keeton et al., J. Biol. Chem., Vol. 266, p. 23048 (1991)). Overexpression of the activated form of TAK1 (TAK1ΔN) results in constitutive activation of a reporter gene containing the luciferase gene under the control of the TGF-β-inducible PAI-1 gene promoter (K. Yamaguchi et al., Science, Vol. 270, p. 2,008 (1995)). We investigated whether overexpression of TAB1 leads to activation of the luciferase reporter gene.

MvlLu cells were transiently transfected by the calcium phosphate method (H. Shibuya et al., Nature, Vol. 357, p. 700 (1992)) using a reporter plasmid p800neoLUC (M. Abe et al., Analyt. Biochem., Vol. 216, p. 276 (1994)) and the TAB1-expressing plasmid pEF-TAB1 or TAK1-encoding expression plasmid (K. Yamaguchi et al., Science, Vol. 270, p. 2008 (1995)). Plasmid pEF-TAB1 contains the full-length TAB1 coding sequence under the control of EF1α promoter, and was constructed by cleaving pEF with EcoRI and inserting the EcoRI fragment from plasmid TABI-f-4.

The plasmid TABI-f-4 was constructed by subcloning TAB1 cDNA at the EcoRI and SmaI sites of pBS. The cells were incubated for 20 hours with and without 30 ng/ml of human TGF-β1, an extract was prepared; and the luciferase was assayed (H. Shibuya et al., Mol. Cell Biol., Vol. 14, p. 5812 (1994)). The luciferase activity was compensated based on expression of β-galactosidase.

Specifically, the transfection efficiency was compensated by simultaneous transfection with pXeX-β-Gal vector (A. D. Johnson et al., Gene, Vol. 147, p. 223 (1994)) in all of the luciferase reporter experiments. Measurement of β-galactosidase was made according to the instructions of the manufacturer (Clontech), using the cell lysate prepared for the luciferase measurement. The luciferase activity was given as the fold-increase with respect to the activity of unstimulated cells transfected with the vector. All of the transfection and luciferase measurements were conducted at least 5 times, with triplicates of each experiment.

The results are shown in FIG. 8. Here, KN indicates the catalytically inactive TAK1-K63W. The data is expressed as the mean±SEM of the luciferase activity from triplicates in a representative experiment overexpression of both TAK1 and TAB1 induced expression of the reporter gene even in the absence of TGF-β, but overexpression of only TAK1 or TAB1 had virtually no effect on the constitutive amount of luciferase activity. These experimental results indicate that TAB1 reinforces TAK1 activity in mammalian cells.

Although overexpression of the TAK1-K63W mutant inhibited TGF-β-stimulated luciferase activity (K. Yamaguchi et al., Science, Vol. 270, p. 2008 (1995)), this is presumably due to sequestering of essential elements in the pathway. On the other hand, overexpression of TAB1 reduces the inhibiting effect of TAK1-K63W, suggesting the possibility that TAB1 is absorbed by overexpression of TAK1-K63W.

Example 10

The 68 C-terminal amino acids of TAB1 [TAB1 (437-5.04)] were sufficient to bind to and activate TAK1, suggesting that the N-terminal domain of TAB1 performs a regulatory role on the function of TAB1. To test this possibility, a shortened form of TAK1 lacking the C-terminal TAK1-binding domain (TAB1 (1-418)) was constructed. MvlLu cells were transiently transfected with p800nedUC reporter and an expression vector coding for TAB8 (1-418) or TAB1 (full-length) in the amounts shown in FIG. 9, and these were complemented with the pEF control vector.

The expression vector coding for TAB1 (1-418) was constructed in the following manner. The 1.3 kb EcoRI-HincII fragment of plasmid TABI-f-4 (containing the TAB1 N-terminal region of amino acids 1-418) was subcloned in pKT10 vector to construct pKT10-TAB1 (1-418). pEF was cleaved with EcoRI and SalI, and the EcoRI-SalI fragment from pKS10-TAB1 (1-418) was inserted therein to construct pEF-TAB1 (1-418).

Next, the cells were incubated for 20 hours with and without 30 ng/ml of human TGF-β1, and the cell lysate was measured for luciferase activity. The values were expressed as fold induction in terms of a percent with respect to the control cells transfected with pEF. No induction of luciferase with TGF-β (1-fold induction) corresponds to 0%. All of the transfection and luciferase measurements were conducted at least 3 times, and a series of 3 of each of the experiments were conducted. The data is expressed as the mean±SEM of the luciferase activities from triplicates in a representative experiment.

The results are shown in FIG. 9. Overexpression of TAB1 (1-418) in MvlLu cells suppressed activity of the reporter gene induced by TGF-β stimulation. Thus, TAB1 (1-418) acts as the dominant negative inhibitor on gene expression induced by TGF-β. These results indicate that TAB1 plays a role in TGF-β signaling.

The mechanism of induction of TAK1 activation by TAK1 believed to be that TAB1 binding to TAK1 induces the necessary conformational changes for activation. Since removal of the 20 N-terminal amino acids of TAK1 causes constitutive activation of the protein kinase, this suggests that the N-terminal domain hinders the catalytic domain, thus inhibiting kinase activity (K. Yamaguchi et al., Science, Vol. 270, p. 2008 (1995)). TABS may eliminate the negative control domain of TAK1 from its catalytic domain. The C-terminus of TAB1 which functions as the TAK1-binding site contains a serine- and threonine-rich region similar to the region found at the N-terminus of TAK1. Therefore, TAB1 is probably an important signaling intermediate between TGF-β and TAK1 MAPKKK.

The invention claimed is:

1. A method for producing a TAB1 protein or a fragment thereof, comprising:

(a) culturing a host that is transformed with a DNA encoding said TAB1 protein or a fragment thereof in a culture medium, wherein said host is a mammalian cell or yeast cell; and (b) isolating the TAB1 protein or fragment thereof from the culture medium wherein said TAB1 protein comprises the amino acid sequence of SEQ ID NO: 1; and wherein said fragment of TAB1 protein comprises the amino acid sequence from the Gin residue at position 437 to the Pro residue at position 504 of SEQ ID NO: 1.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1560 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 30..1541

(ix) FEATURE:
    (A) NAME/KEY: mat_peptide
    (B) LOCATION: 30..1541

(xi) SEQUENCE DESCRIPTION: SEQ ID NO: 1:

```
GAATTCGTGG CCCGCAGGGT TCCTCCAAG ATG GCG GCG CAG AGG AGG AGC TTG          53
                                Met Ala Ala Gln Arg Arg Ser Leu
                                  1               5

CTG CAG AGT GAG CAG CAG CCA AGC TGG ACA GAT GAC CTG CCT CTC TGC         101
Leu Gln Ser Glu Gln Gln Pro Ser Trp Thr Asp Asp Leu Pro Leu Cys
         10                  15                  20

CAC CTC TCT GGG GTT GGC TCA GCC TCC AAC CGC AGC TAC TCT GCT GAT         149
His Leu Ser Gly Val Gly Ser Ala Ser Asn Arg Ser Tyr Ser Ala Asp
 25                  30                  35                  40

GGC AAG GGC ACT GAG AGC CAC CCG CCA GAG GAC AGC TGG CTC AAG TTC         197
Gly Lys Gly Thr Glu Ser His Pro Pro Glu Asp Ser Trp Leu Lys Phe
                 45                  50                  55

AGG AGT GAG AAC AAC TGC TTC CTG TAT GGG GTC TTC AAC GGC TAT GAT         245
Arg Ser Glu Asn Asn Cys Phe Leu Tyr Gly Val Phe Asn Gly Tyr Asp
                     60                  65                  70

GGC AAC CGA GTG ACC AAC TTC GTG GCC CAG CGG CTG TCC GCA GAG CTC         293
Gly Asn Arg Val Thr Asn Phe Val Ala Gln Arg Leu Ser Ala Glu Leu
             75                  80                  85

CTG CTG GGC CAG CTG AAT GCC GAG CAC GCC GAG GCC GAT GTG CGG CGT         341
Leu Leu Gly Gln Leu Asn Ala Glu His Ala Glu Ala Asp Val Arg Arg
         90                  95                 100

GTG CTG CTG CAG GCC TTC GAT GTG GTG GAG AGG AGC TTC CTG GAG TCC         389
Val Leu Leu Gln Ala Phe Asp Val Val Glu Arg Ser Phe Leu Glu Ser
105                 110                 115                 120

ATT GAC GAC GCC TTG GCT GAG AAG GCA AGC CTC CAG TCG CAA TTG CCA         437
Ile Asp Asp Ala Leu Ala Glu Lys Ala Ser Leu Gln Ser Gln Leu Pro
                125                 130                 135

GAG GGA GTC CCT CAG CAC CAG CTG CCT CCT CAG TAT CAG AAG ATC CTT         485
Glu Gly Val Pro Gln His Gln Leu Pro Pro Gln Tyr Gln Lys Ile Leu
                140                 145                 150

GAG AGA CTC AAG ACG TTA GAG AGG GAA ATT TCG GGA GGG GCC ATG GCC         533
Glu Arg Leu Lys Thr Leu Glu Arg Glu Ile Ser Gly Gly Ala Met Ala
            155                 160                 165

GTT GTG GCG GTC CTT CTC AAC AAC AAG CTC TAC GTC GCC AAT GTC GGT         581
Val Val Ala Val Leu Leu Asn Asn Lys Leu Tyr Val Ala Asn Val Gly
        170                 175                 180

ACA AAC CGT GCA CTT TTA TGC AAA TCG ACA GTG GAT GGG TTG CAG GTG         629
Thr Asn Arg Ala Leu Leu Cys Lys Ser Thr Val Asp Gly Leu Gln Val
185                 190                 195                 200

ACA CAG CTG AAC GTG GAC CAC ACC ACA GAG AAC GAG GAT GAG CTC TTC         677
Thr Gln Leu Asn Val Asp His Thr Thr Glu Asn Glu Asp Glu Leu Phe
                205                 210                 215

CGT CTT TCG CAG CTG GGC TTG GAT GCT GGA AAG ATC AAG CAG GTG GGG         725
Arg Leu Ser Gln Leu Gly Leu Asp Ala Gly Lys Ile Lys Gln Val Gly
                220                 225                 230

ATC ATC TGT GGG CAG GAG AGC ACC CGG CGG ATC GGG GAT TAC AAG GTT         773
Ile Ile Cys Gly Gln Glu Ser Thr Arg Arg Ile Gly Asp Tyr Lys Val
            235                 240                 245

AAA TAT GGC TAC ACG GAC ATT GAC CTT CTC AGC GCT GCC AAG TCC AAA         821
Lys Tyr Gly Tyr Thr Asp Ile Asp Leu Leu Ser Ala Ala Lys Ser Lys
        250                 255                 260

CCA ATC ATC GCA GAG CCA GAA ATC CAT GGG GCA CAG CCG CTG GAT GGG         869
Pro Ile Ile Ala Glu Pro Glu Ile His Gly Ala Gln Pro Leu Asp Gly
265                 270                 275                 280
```

-continued

```
GTG ACG GGC TTC TTG GTG CTG ATG TCG GAG GGG TTG TAC AAG GCC CTA      917
Val Thr Gly Phe Leu Val Leu Met Ser Glu Gly Leu Tyr Lys Ala Leu
            285                 290                 295

GAG GCA GCC CAT GGG CCT GGG CAG GCC AAC CAG GAG ATT GCT GCG ATG      965
Glu Ala Ala His Gly Pro Gly Gln Ala Asn Gln Glu Ile Ala Ala Met
        300                 305                 310

ATT GAC ACT GAG TTT GCC AAG CAG ACC TCC CTG GAC GCA GTG GCC CAG     1013
Ile Asp Thr Glu Phe Ala Lys Gln Thr Ser Leu Asp Ala Val Ala Gln
        315                 320                 325

GCC GTC GTG GAC CGG GTG AAG CGC ATC CAC AGC GAC ACC TTC GCC AGT     1061
Ala Val Val Asp Arg Val Lys Arg Ile His Ser Asp Thr Phe Ala Ser
        330                 335                 340

GGT GGG GAG CGT GCC AGG TTC TGC CCC CGG CAC GAG GAC ATG ACC CTG     1109
Gly Gly Glu Arg Ala Arg Phe Cys Pro Arg His Glu Asp Met Thr Leu
345                 350                 355                 360

CTA GTG AGG AAC TTT GGC TAC CCG CTG GGC GAA ATG AGC CAG CCC ACA     1157
Leu Val Arg Asn Phe Gly Tyr Pro Leu Gly Glu Met Ser Gln Pro Thr
                365                 370                 375

CCG AGC CCA GCC CCA GCT GCA GGA GGA CGA GTG TAC CCT GTG TCT GTG     1205
Pro Ser Pro Ala Pro Ala Ala Gly Gly Arg Val Tyr Pro Val Ser Val
            380                 385                 390

CCA TAC TCC AGC GCC CAG AGC ACC AGC AAG ACC AGC GTG ACC CTC TCC     1253
Pro Tyr Ser Ser Ala Gln Ser Thr Ser Lys Thr Ser Val Thr Leu Ser
                395                 400                 405

CTT GTC ATG CCC TCC CAG GGC CAG ATG GTC AAC GGG GCT CAC AGT GCT     1301
Leu Val Met Pro Ser Gln Gly Gln Met Val Asn Gly Ala His Ser Ala
            410                 415                 420

TCC ACC CTG GAC GAA GCC ACC CCC ACC CTC ACC AAC CAA AGC CCG ACC     1349
Ser Thr Leu Asp Glu Ala Thr Pro Thr Leu Thr Asn Gln Ser Pro Thr
425                 430                 435                 440

TTA ACC CTG CAG TCC ACC AAC ACG CAC ACG CAG AGC AGC AGC TCC AGC     1397
Leu Thr Leu Gln Ser Thr Asn Thr His Thr Gln Ser Ser Ser Ser Ser
                445                 450                 455

TCT GAC GGA GGC CTC TTC CGC TCC CGG CCC GCC CAC TCG CTC CCG CCT     1445
Ser Asp Gly Gly Leu Phe Arg Ser Arg Pro Ala His Ser Leu Pro Pro
            460                 465                 470

GGC GAG GAC GGT CGT GTT GAG CCC TAT GTG GAC TTT GCT GAG TTT TAC     1493
Gly Glu Asp Gly Arg Val Glu Pro Tyr Val Asp Phe Ala Glu Phe Tyr
            475                 480                 485

CGC CTC TGG AGC GTG GAC CAT GGC GAG CAG AGC GTG GTG ACA GCA CCG     1541
Arg Leu Trp Ser Val Asp His Gly Glu Gln Ser Val Val Thr Ala Pro
490                 495                 500

TAGGGCAGCC GGAGGAATG                                                 1560
```

(2) INFORMATION FOR SEQ ID NO: 2:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ala Gln Arg Arg Ser Leu Leu Gln Ser Glu Gln Gln Pro Ser
  1               5                  10                  15

Trp Thr Asp Asp Leu Pro Leu Cys His Leu Ser Gly Val Gly Ser Ala
                20                  25                  30

Ser Asn Arg Ser Tyr Ser Ala Asp Gly Lys Gly Thr Glu Ser His Pro
            35                  40                  45
```

-continued

```
Pro Glu Asp Ser Trp Leu Lys Phe Arg Ser Glu Asn Asn Cys Phe Leu
    50                  55                  60
Tyr Gly Val Phe Asn Gly Tyr Asp Gly Asn Arg Val Thr Asn Phe Val
65                  70                  75                  80
Ala Gln Arg Leu Ser Ala Glu Leu Leu Gly Gln Leu Asn Ala Glu
                    85                  90                  95
His Ala Glu Ala Asp Val Arg Arg Val Leu Leu Gln Ala Phe Asp Val
                100                 105                 110
Val Glu Arg Ser Phe Leu Glu Ser Ile Asp Asp Ala Leu Ala Glu Lys
                115                 120                 125
Ala Ser Leu Gln Ser Gln Leu Pro Glu Gly Val Pro Gln His Gln Leu
            130                 135                 140
Pro Pro Gln Tyr Gln Lys Ile Leu Glu Arg Leu Lys Thr Leu Glu Arg
145                 150                 155                 160
Glu Ile Ser Gly Gly Ala Met Ala Val Ala Val Leu Leu Asn Asn
                    165                 170                 175
Lys Leu Tyr Val Ala Asn Val Gly Thr Asn Arg Ala Leu Leu Cys Lys
                180                 185                 190
Ser Thr Val Asp Gly Leu Gln Val Thr Gln Leu Asn Val Asp His Thr
            195                 200                 205
Thr Glu Asn Glu Asp Glu Leu Phe Arg Leu Ser Gln Leu Gly Leu Asp
        210                 215                 220
Ala Gly Lys Ile Lys Gln Val Gly Ile Ile Cys Gly Gln Glu Ser Thr
225                 230                 235                 240
Arg Arg Ile Gly Asp Tyr Lys Val Lys Tyr Gly Tyr Thr Asp Ile Asp
                    245                 250                 255
Leu Leu Ser Ala Ala Lys Ser Lys Pro Ile Ile Ala Glu Pro Glu Ile
                260                 265                 270
His Gly Ala Gln Pro Leu Asp Gly Val Thr Gly Phe Leu Val Leu Met
        275                 280                 285
Ser Glu Gly Leu Tyr Lys Ala Leu Glu Ala Ala His Gly Pro Gly Gln
    290                 295                 300
Ala Asn Gln Glu Ile Ala Ala Met Ile Asp Thr Glu Phe Ala Lys Gln
305                 310                 315                 320
Thr Ser Leu Asp Ala Val Ala Gln Ala Val Val Asp Arg Val Lys Arg
                    325                 330                 335
Ile His Ser Asp Thr Phe Ala Ser Gly Gly Glu Arg Ala Arg Phe Cys
                340                 345                 350
Pro Arg His Glu Asp Met Thr Leu Leu Val Arg Asn Phe Gly Tyr Pro
        355                 360                 365
Leu Gly Glu Met Ser Gln Pro Thr Pro Ser Pro Ala Pro Ala Ala Gly
    370                 375                 380
Gly Arg Val Tyr Pro Val Ser Val Pro Tyr Ser Ser Ala Gln Ser Thr
385                 390                 395                 400
Ser Lys Thr Ser Val Thr Leu Ser Leu Val Met Pro Ser Gln Gly Gln
                    405                 410                 415
Met Val Asn Gly Ala His Ser Ala Ser Thr Leu Asp Glu Ala Thr Pro
                420                 425                 430
Thr Leu Thr Asn Gln Ser Pro Thr Leu Thr Leu Gln Ser Thr Asn Thr
        435                 440                 445
His Thr Gln Ser Ser Ser Ser Ser Asp Gly Gly Leu Phe Arg Ser
    450                 455                 460
Arg Pro Ala His Ser Leu Pro Pro Gly Glu Asp Gly Arg Val Glu Pro
```

```
                   465                 470                 475                 480
Tyr Val Asp Phe Ala Glu Phe Tyr Arg Leu Trp Ser Val Asp His Gly
                        485                 490                 495

Glu Gln Ser Val Val Thr Ala Pro
            500

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 3:

GAGAATTCAT GCGGCAAAGC                                                          20

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 4:

GGGTCGACTA CGGTGC                                                              16

(2) INFORMATION FOR SEQ ID NO: 5:

(i) SEQUENCE CHARACTERISTICS:
        (A) LENGTH: 1560 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 30..1541

(ix) FEATURE:
        (A) NAME/KEY: mat_peptide
        (B) LOCATION: 30..1541

(xi) SEQUENCE DESCRIPTION: SEQ ID NO: 5:

GAATTCGTGG CCCGCAGGGT TCCTCCAAG ATG GCG GCG CAG AGG AGG AGC TTG             53
                                 Met Ala Ala Gln Arg Arg Ser Leu
                                   1               5

CTG CAG AGT GAG CAG CAG CCA AGC TGG ACA GAT GAC CTG CCT CTC TGC            101
Leu Gln Ser Glu Gln Gln Pro Ser Trp Thr Asp Asp Leu Pro Leu Cys
     10                  15                  20

CAC CTC TCT GGG GTT GGC TCA GCC TCC AAC CGC AGC TAC TCT GCT GAT            149
His Leu Ser Gly Val Gly Ser Ala Ser Asn Arg Ser Tyr Ser Ala Asp
 25                  30                  35                  40

GGC AAG GGC ACT GAG AGC CAC CCG CCA GAG GAC AGA TGG CTC AAG TTC            197
Gly Lys Gly Thr Glu Ser His Pro Pro Glu Asp Arg Trp Leu Lys Phe
                 45                  50                  55

AGG AGT GAG AAC AAC TGC TTC CTG TAT GGG GTC TTC AAC GGC TAT GAT            245
Arg Ser Glu Asn Asn Cys Phe Leu Tyr Gly Val Phe Asn Gly Tyr Asp
             60                  65                  70

GGC AAC CGA GTG ACC AAC TTC GTG GCC CAG CGG CTG TCC GCA GAG CTC            293
Gly Asn Arg Val Thr Asn Phe Val Ala Gln Arg Leu Ser Ala Glu Leu
         75                  80                  85

CTG CTG GGC CAG CTG AAT GCC GAG CAC GCC GAG GCC GAT GTG CGG CGT            341
Leu Leu Gly Gln Leu Asn Ala Glu His Ala Glu Ala Asp Val Arg Arg
```

-continued

```
            90                  95                 100
GTG CTG CTG CAG GCC TTC GAT GTG GTG GAG AGG AGC TTC CTG GAG TCC        389
Val Leu Leu Gln Ala Phe Asp Val Val Glu Arg Ser Phe Leu Glu Ser
105                 110                 115                 120

ATT GAC GAC GCC TTG GCT GAG AAG GCA AGC CTC CAG TCG CAA TTG CCA        437
Ile Asp Asp Ala Leu Ala Glu Lys Ala Ser Leu Gln Ser Gln Leu Pro
            125                 130                 135

GAG GGA GTC CCT CAG CAC CAG CTG CCT CCT CAG TAT CAG AAG ATC CTT        485
Glu Gly Val Pro Gln His Gln Leu Pro Pro Gln Tyr Gln Lys Ile Leu
                140                 145                 150

GAG AGA CTC AAG ACG TTA GAG AGG GAA ATT TCG GGA GGG GCC ATG GCC        533
Glu Arg Leu Lys Thr Leu Glu Arg Glu Ile Ser Gly Gly Ala Met Ala
            155                 160                 165

GTT GTG GCG GTC CTT CTC AAC AAC AAG CTC TAC GTC GCC AAT GTC GGT        581
Val Val Ala Val Leu Leu Asn Asn Lys Leu Tyr Val Ala Asn Val Gly
        170                 175                 180

ACA AAC CGT GCA CTT TTA TGC AAA TCG ACA GTG GAT GGG TTG CAG GTG        629
Thr Asn Arg Ala Leu Leu Cys Lys Ser Thr Val Asp Gly Leu Gln Val
185                 190                 195                 200

ACA CAG CTG AAC GTG GAC CAC ACC ACA GAG AAC GAG GAT GAG CTC TTC        677
Thr Gln Leu Asn Val Asp His Thr Thr Glu Asn Glu Asp Glu Leu Phe
                205                 210                 215

CGT CTT TCG CAG CTG GGC TTG GAT GCT GGA AAG ATC AAG CAG GTG GGG        725
Arg Leu Ser Gln Leu Gly Leu Asp Ala Gly Lys Ile Lys Gln Val Gly
            220                 225                 230

ATC ATC TGT GGG CAG GAG AGC ACC CGG CGG ATC GGG GAT TAC AAG GTT        773
Ile Ile Cys Gly Gln Glu Ser Thr Arg Arg Ile Gly Asp Tyr Lys Val
        235                 240                 245

AAA TAT GGC TAC ACG GAC ATT GAC CTT CTC AGC GCT GCC AAG TCC AAA        821
Lys Tyr Gly Tyr Thr Asp Ile Asp Leu Leu Ser Ala Ala Lys Ser Lys
250                 255                 260

CCA ATC ATC GCA GAG CCA GAA ATC CAT GGG GCA CAG CCG CTG GAT GGG        869
Pro Ile Ile Ala Glu Pro Glu Ile His Gly Ala Gln Pro Leu Asp Gly
265                 270                 275                 280

GTG ACG GGC TTC TTG GTG CTG ATG TCG GAG GGG TTG TAC AAG GCC CTA        917
Val Thr Gly Phe Leu Val Leu Met Ser Glu Gly Leu Tyr Lys Ala Leu
                285                 290                 295

GAG GCA GCC CAT GGG CCT GGG CAG GCC AAC CAG GAG ATT GCT GCG ATG        965
Glu Ala Ala His Gly Pro Gly Gln Ala Asn Gln Glu Ile Ala Ala Met
            300                 305                 310

ATT GAC ACT GAG TTT GCC AAG CAG ACC TCC CTG GAC GCA GTG GCC CAG       1013
Ile Asp Thr Glu Phe Ala Lys Gln Thr Ser Leu Asp Ala Val Ala Gln
        315                 320                 325

GCC GTC GTG GAC CGG GTG AAG CGC ATC CAC AGC GAC ACC TTC GCC AGT       1061
Ala Val Val Asp Arg Val Lys Arg Ile His Ser Asp Thr Phe Ala Ser
330                 335                 340

GGT GGG GAG CGT GCC AGG TTC TGC CCC CGG CAC GAG GAC ATG ACC CTG       1109
Gly Gly Glu Arg Ala Arg Phe Cys Pro Arg His Glu Asp Met Thr Leu
345                 350                 355                 360

CTA GTG AGG AAC TTT GGC TAC CCG CTG GGC GAA ATG AGC CAG CCC ACA       1157
Leu Val Arg Asn Phe Gly Tyr Pro Leu Gly Glu Met Ser Gln Pro Thr
                365                 370                 375

CCG AGC CCA GCC CCA GCT GCA GGA GGA CGA GTG TAC CCT GTG TCT GTG       1205
Pro Ser Pro Ala Pro Ala Ala Gly Gly Arg Val Tyr Pro Val Ser Val
            380                 385                 390

CCA TAC TCC AGC GCC CAG AGC ACC AGC AAG ACC AGC GTG ACC CTC TCC       1253
Pro Tyr Ser Ser Ala Gln Ser Thr Ser Lys Thr Ser Val Thr Leu Ser
        395                 400                 405

CTT GTC ATG CCC TCC CAG GGC CAG ATG GTC AAC GGG GCT CAC AGT GCT       1301
```

```
Leu Val Met Pro Ser Gln Gly Gln Met Val Asn Gly Ala His Ser Ala
    410                 415                 420

TCC ACC CTG GAC GAA GCC ACC CCC ACC CTC ACC AAC CAA AGC CCG ACC      1349
Ser Thr Leu Asp Glu Ala Thr Pro Thr Leu Thr Asn Gln Ser Pro Thr
425                 430                 435                 440

TTA ACC CTG CAG TCC ACC AAC ACG CAC ACG CAG AGC AGC AGC TCC AGC      1397
Leu Thr Leu Gln Ser Thr Asn Thr His Thr Gln Ser Ser Ser Ser Ser
                445                 450                 455

TCT GAC GGA GGC CTC TTC CGC TCC CGG CCC GCC CAC TCG CTC CCG CCT      1445
Ser Asp Gly Gly Leu Phe Arg Ser Arg Pro Ala His Ser Leu Pro Pro
            460                 465                 470

GGC GAG GAC GGT CGT GTT GAG CCC TAT GTG GAC TTT GCT GAG TTT TAC      1493
Gly Glu Asp Gly Arg Val Glu Pro Tyr Val Asp Phe Ala Glu Phe Tyr
                475                 480                 485

CGC CTC TGG AGC GTG GAC CAT GGC GAG CAG AGC GTG GTG ACA GCA CCG      1541
Arg Leu Trp Ser Val Asp His Gly Glu Gln Ser Val Val Thr Ala Pro
490                 495                 500

TAGGGCAGCC GGAGGAATG                                                  1560
```

(2) INFORMATION FOR SEQ ID NO: 6:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ala Ala Gln Arg Arg Ser Leu Leu Gln Ser Glu Gln Gln Pro Ser
1               5                   10                  15

Trp Thr Asp Asp Leu Pro Leu Cys His Leu Ser Gly Val Gly Ser Ala
                20                  25                  30

Ser Asn Arg Ser Tyr Ser Ala Asp Gly Lys Gly Thr Glu Ser His Pro
            35                  40                  45

Pro Glu Asp Arg Trp Leu Lys Phe Arg Ser Glu Asn Asn Cys Phe Leu
        50                  55                  60

Tyr Gly Val Phe Asn Gly Tyr Asp Gly Asn Arg Val Thr Asn Phe Val
65                  70                  75                  80

Ala Gln Arg Leu Ser Ala Glu Leu Leu Gly Gln Leu Asn Ala Glu
                85                  90                  95

His Ala Glu Ala Asp Val Arg Arg Val Leu Leu Gln Ala Phe Asp Val
            100                 105                 110

Val Glu Arg Ser Phe Leu Glu Ser Ile Asp Asp Ala Leu Ala Glu Lys
        115                 120                 125

Ala Ser Leu Gln Ser Gln Leu Pro Glu Gly Val Pro Gln His Gln Leu
130                 135                 140

Pro Pro Gln Tyr Gln Lys Ile Leu Glu Arg Leu Lys Thr Leu Glu Arg
145                 150                 155                 160

Glu Ile Ser Gly Gly Ala Met Ala Val Val Ala Val Leu Leu Asn Asn
                165                 170                 175

Lys Leu Tyr Val Ala Asn Val Gly Thr Asn Arg Ala Leu Leu Cys Lys
            180                 185                 190

Ser Thr Val Asp Gly Leu Gln Val Thr Gln Leu Asn Val Asp His Thr
        195                 200                 205

Thr Glu Asn Glu Asp Glu Leu Phe Arg Leu Ser Gln Leu Gly Leu Asp
    210                 215                 220
```

-continued

```
Ala Gly Lys Ile Lys Gln Val Gly Ile Ile Cys Gly Gln Glu Ser Thr
225                 230                 235                 240

Arg Arg Ile Gly Asp Tyr Lys Val Lys Tyr Gly Tyr Thr Asp Ile Asp
            245                 250                 255

Leu Leu Ser Ala Ala Lys Ser Lys Pro Ile Ile Ala Glu Pro Glu Ile
        260                 265                 270

His Gly Ala Gln Pro Leu Asp Gly Val Thr Gly Phe Leu Val Leu Met
    275                 280                 285

Ser Glu Gly Leu Tyr Lys Ala Leu Glu Ala Ala His Gly Pro Gly Gln
290                 295                 300

Ala Asn Gln Glu Ile Ala Ala Met Ile Asp Thr Glu Phe Ala Lys Gln
305                 310                 315                 320

Thr Ser Leu Asp Ala Val Ala Gln Ala Val Val Asp Arg Val Lys Arg
                325                 330                 335

Ile His Ser Asp Thr Phe Ala Ser Gly Gly Glu Arg Ala Arg Phe Cys
            340                 345                 350

Pro Arg His Glu Asp Met Thr Leu Leu Val Arg Asn Phe Gly Tyr Pro
        355                 360                 365

Leu Gly Glu Met Ser Gln Pro Thr Pro Ser Pro Ala Pro Ala Ala Gly
    370                 375                 380

Gly Arg Val Tyr Pro Val Ser Val Pro Tyr Ser Ser Ala Gln Ser Thr
385                 390                 395                 400

Ser Lys Thr Ser Val Thr Leu Ser Leu Val Met Pro Ser Gln Gly Gln
                405                 410                 415

Met Val Asn Gly Ala His Ser Ala Ser Thr Leu Asp Glu Ala Thr Pro
            420                 425                 430

Thr Leu Thr Asn Gln Ser Pro Thr Leu Thr Leu Gln Ser Thr Asn Thr
        435                 440                 445

His Thr Gln Ser Ser Ser Ser Ser Asp Gly Gly Leu Phe Arg Ser
    450                 455                 460

Arg Pro Ala His Ser Leu Pro Pro Gly Glu Asp Gly Arg Val Glu Pro
465                 470                 475                 480

Tyr Val Asp Phe Ala Glu Phe Tyr Arg Leu Trp Ser Val Asp His Gly
                485                 490                 495

Glu Gln Ser Val Val Thr Ala Pro
            500
```

(2) INFORMATION FOR SEQ ID NO: 7:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 7:

```
Met Ser Thr Ala Ser Ala Ala Ser Ser Ser Ser Ser Ser Ala Ser
1               5                   10                  15

Glu Met Ile Glu Ala Pro Ser Gln
            20
```

(2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 8:

Leu Glu Gln Lys Leu Ile Ser Glu Glu Asp Leu Asn
1               5                   10